United States Patent
Hirao et al.

(10) Patent No.: US 9,700,847 B2
(45) Date of Patent: Jul. 11, 2017

(54) COMBINED CHLORINE AGENT AND PRODUCTION AND USE THEREOF

(75) Inventors: Takanori Hirao, Tokyo (JP); Tetsuya Aoki, Tokyo (JP)

(73) Assignee: KURITA WATER INDUSTRIES, LTD., Shinjuku-ku, Tokyo (JP)

( * ) Notice: Subject to any disclaimer, the term of this patent is extended or adjusted under 35 U.S.C. 154(b) by 312 days.

(21) Appl. No.: 13/637,521

(22) PCT Filed: Mar. 30, 2011

(86) PCT No.: PCT/JP2011/058067
§ 371 (c)(1),
(2), (4) Date: Sep. 26, 2012

(87) PCT Pub. No.: WO2011/125762
PCT Pub. Date: Oct. 13, 2011

(65) Prior Publication Data
US 2013/0026097 A1   Jan. 31, 2013

(30) Foreign Application Priority Data
Mar. 31, 2010   (JP) .................................. 2010-083959

(51) Int. Cl.
*C02F 5/00*   (2006.01)
*C02F 1/44*   (2006.01)
(Continued)

(52) U.S. Cl.
CPC ............ *B01D 65/08* (2013.01); *A01N 41/08* (2013.01); *A01N 59/00* (2013.01); *C02F 1/441* (2013.01);
(Continued)

(58) Field of Classification Search
USPC .................. 210/749, 753, 754, 756
See application file for complete search history.

(56) References Cited

U.S. PATENT DOCUMENTS

| | | | |
|---|---|---|---|
| 4,992,195 A | 2/1991 | Dolan et al. | |
| 6,290,856 B1 * | 9/2001 | Beall | ............................. 210/753 |

(Continued)

FOREIGN PATENT DOCUMENTS

| | | |
|---|---|---|
| CN | 1406484 A | 4/2003 |
| CN | 1646011 A | 7/2005 |

(Continued)

OTHER PUBLICATIONS

European Patent Office Search Report dated Nov. 26, 2013 (7 pages).

(Continued)

*Primary Examiner* — Krishnan S Menon
*Assistant Examiner* — Ryan B Huang
(74) *Attorney, Agent, or Firm* — Flynn, Thiel, Boutell & Tanis, P.C.

(57) ABSTRACT

A combined chlorine agent having a low concentration of free chlorine and a high concentration of combined chlorine whereby the combined chlorine concentration of water can be increased when added to water systems at a low concentration of free chlorine. The combined chlorine agent is an aqueous agent which contains an alkali metal hydroxide, sulfamic acid, and an oxidizing agent based on chlorine, wherein the compositional ratio of the oxidizing agent based on chlorine to the sulfamic acid is in the range from 0.45 to 0.6 by Cl/N (mole ratio), the compositional ratio of the oxidizing agent based on chlorine to alkali is in the range from 0.3 to 0.4 by Cl/alkali metal (mole ratio), and the free chlorine concentration in the aqueous agent is 2% by weight or lower of the total chlorine concentration.

5 Claims, 7 Drawing Sheets

(51) Int. Cl.
*B01D 65/08* (2006.01)
*A01N 41/08* (2006.01)
*A01N 59/00* (2006.01)
*C02F 1/76* (2006.01)
*B01D 61/02* (2006.01)
*C02F 103/02* (2006.01)

(52) U.S. Cl.
CPC .............. *C02F 1/76* (2013.01); *B01D 61/025* (2013.01); *B01D 2321/10* (2013.01); *B01D 2321/168* (2013.01); *C02F 2103/023* (2013.01); *C02F 2303/04* (2013.01); *C02F 2303/16* (2013.01); *C02F 2303/20* (2013.01)

(56) References Cited

U.S. PATENT DOCUMENTS

| | | | |
|---|---|---|---|
| 6,471,974 | B1 | 10/2002 | Rees et al. |
| 7,285,221 | B2* | 10/2007 | Tsuneki et al. ............... 210/701 |
| 7,341,671 | B2 | 3/2008 | Shim et al. |
| 2005/0147528 | A1 | 7/2005 | Shim et al. |
| 2006/0054563 | A1 | 3/2006 | Tsuneki et al. |
| 2006/0089285 | A1 | 4/2006 | Ahmed et al. |
| 2010/0206809 | A1* | 8/2010 | Ikuno ..................... B01D 61/08 210/638 |

FOREIGN PATENT DOCUMENTS

| | | |
|---|---|---|
| CN | 1655676 A | 8/2005 |
| EP | 1 287 741 A1 | 3/2003 |
| JP | 2003-503323 A | 1/2003 |
| JP | 2003-146817 | 5/2003 |
| JP | 2003-267811 | 9/2003 |
| JP | 2005-519089 | 6/2005 |
| JP | 2006-263510 | 10/2006 |
| JP | 2006263510 A * | 10/2006 |
| JP | 2009-084163 | 4/2009 |
| JP | 2009-195823 A | 9/2009 |
| JP | 2010-58079 A | 3/2010 |
| JP | 2010-063998 A | 3/2010 |
| WO | WO 03/096810 A1 | 11/2003 |

OTHER PUBLICATIONS

Letter from Singapore Patent Office dated Nov. 7, 2013 with Singapore Written Opinion dated Oct. 18, 2013 and Singapore Search Report dated Oct. 2, 2013 (12 pgs.).
Koch Membrane Systems Fluid Systems TFC—HR 8" Elements, High Rejection, Low Pressure RO Elements for Brackish Water, Oct. 2008 (2 pages).
PCT/JP2011/058067 International Search Report (2 pgs.).
Response to Japanese Patent Office issued in Application No. 2012-509525 with extracted translation dated Feb. 3, 2015 (29 pages).
Examination Report of Taiwan Patent Office in Application No. 100111044 with extracted translation dated Feb. 12, 2015 (7 pages).
English translation of Decision for Patent Grant of Japanese Patent Office in Application No. 2012-509525 dated Feb. 26, 2015 (6 pages).
Reference 1, Principles of Chemistry, Keith J. Laidler (Harcourt, Brace & World, New York on 1966) (14 pages).
Primary Notification of Examination Report of Chinese Patent Office issued in Application No. 201180016638.9 with extracted translation dated Sep. 24, 2013 (10 pages).
Response to Written Opinion of Singapore Patent Office issued in Application No. 2012072567 dated Apr. 2, 2014 (9 pages).
Response to Primary Notification of Examination Report of Chinese Patent Office issued in Application No. 201180016638.9 sent Sep. 24, 2013 with extracted translation (42 pages).
Response to Search Report Opinion of the European Patent Office issued in Application No. 11765662.9 dated Jun. 6, 2014 (10 pages).
Search and Examination Report of Intellectual Property Office of Singapore issued in Application No. 2012072567 dated Jul. 22, 2014 (7 pages).
Secondary Notification of Examination Report of Chinese Patent Office issued in Application No. 201180016638.9 with extracted translation dated Jul. 30, 2014 (5 pages).
Office Action of Japanese Patent Office issued in Application No. 2012-509526 with English translation dated Dec. 9, 2014 (5 pages).
Response to Secondary Notification of Examination Report of Chinese Patent Office issued in Application No. 201180016638.9 sent Jul. 30, 2014 with extracted translation dated Dec. 11, 2014 (39 pages).
CN Office Action for corresponding application No. 201180016638.9, dated Apr. 1, 2015, with partial English translation (5 pgs.).
CN Response for corresponding application No. 201180016638.9, dated Jun. 16, 2015, with partial English translation (30 pgs.).
CN Notice of Allowance for corresponding application No. 201180016638.9, dated Oct. 10, 2015, with partial English translation (4 pgs.).
EP Office Action for corresponding application No. 11 765 662.9, dated Sep. 4, 2015 (6 pgs.).
EP Response for corresponding application No. 11 765 662.9, dated Nov. 30, 2015 (8 pgs.).
EP Notice of Allowance for corresponding application No. 11 765 662.9, dated Mar. 31, 2016 (40 pgs.).
TW Response for corresponding application No. 100111044, dated Jun. 23, 2015, with partial English translation (29 pgs.).
TW Notice of Allowance for corresponding application No. 100111044, dated Mar. 8, 2016, with partial English translation (3 pgs.).
KR Amendment for corresponding application No. 10-2012-7024906, dated Mar. 23, 2016, with partial English translation (9 pgs.).
KR Office Action for corresponding application No. 10-2012-7024906, dated Apr. 29, 2016, with partial English translation (8 pgs.).
KR Response for corresponding application No. 10-2012-7024906, dated Jun. 29, 2016, with partial English translation (43 pgs.).
KR Notice of Allowance for corresponding application No. 10-2012-7024906, dated Aug. 3, 2016, with partial English translation (3 pgs.).

* cited by examiner

COMBINED CHLORINE AGENT AND PRODUCTION AND USE THEREOF

TECHNICAL FIELD

The present invention relates to a combined chlorine agent used suitably for a slime control agent of a reverse osmosis membrane (in the following sometimes called as "RO membrane") and methods of production and use thereof. More specifically, the present invention relates to a combined chlorine agent having a low concentration of free chlorine and a high concentration of combined chlorine, to a method of efficient production thereof and a method of chlorine treatment using the combined chlorine agent.

TECHNICAL BACKGROUND

Since a RO membrane reveals a high rejection rate of solute, clear permeate obtained by a RO membrane treatment has a superior water quality and can be reused effectively for a variety of purposes. If, however, water to be treated contains contaminants such as suspended solids and organic substances which foul the RO membrane, there is a problem wherein the RO membrane is contaminated by these contaminants causing declines of flux and rejection rate as the treatment lasts.

In water treatment using a RO membrane, a method continuing a stable operation by averting obstructions such as a decline of flux and increase of operational pressure in a RO membrane apparatus is performed by adopting pretreatment (including coagulation, solid-liquid separation and active carbon treatment) to clarify feed water to the RO membrane, wherein, in order to prevent fouling of the RO membrane and to obtain a high treatment efficiency, the feed water to the RO membrane apparatus is evaluated by a Fouling Index (FI) as set forth in JIS K3802, or Silt Density Index (SDI) as set forth in ASTM D4189, and the pretreatment is carried out wherein the FI or SDI falls in a predetermined value or lower, for instance, the FI or SDI becomes 3-4 or lower.

In a cooling water circulation system, a part of the water evaporates when the cooling water used for cooling a heat source is cooled in a cooling tower, whereby contaminants such as suspended solids and organic substances are condensed. Further, to the cooling water, bacteria which cause slime formation mix from the outer side and slime formed in the cooling tower mix by exfoliating, so that sterilization for slime control becomes necessary. Since, even if contaminants such as suspended solids and organic substances have been removed, bacteria contained in the water to be treated proliferate on the surface of the RO membrane to decrease the flux of the permeate, sterilization of the water to be treated is performed by adding a sterilizer to prevent fouling of the membrane by the proliferation of bacteria.

As a sterilizer for general water systems, a free chlorine agent such as chlorine and sodium hypochlorite is widely used which causes, as an oxidizing agent, the deterioration of the RO membrane and a decline in efficiency. In order to ease the oxidizing effect, Patent Document 1 (JP H01-104310A) proposes the formation of a chloramine by adding ammonium ion after sterilization by a free chlorine agent. However, Patent Document 1 does not disclose the application to water to be treated containing the contaminant in detail, for instance, when and how it is applied.

Patent document 2 (JP2006-263510A) teaches a slime control agent for membrane separation which comprises a combined chlorine agent comprising an oxidizing agent based on chlorine and a sulfamic compound. Patent document 2 also teaches that free chlorine is contained in a specific ratio to the above combined chlorine agent which is added into the water to be treated, and that there is a correlation similar to equilibrium. In order to obtain the sterilizing effect, the above combined chlorine agent is to be used in a concentration wherein free chlorine is detected in the water to be treated, while the combined chlorine agent is used in a concentration wherein the free chlorine concentration is 2-6 mg/L and total chlorine concentration is 20-60 mg/L in the Examples.

Since there are problems that a RO membrane, especially a RO membrane composed of a high molecular weight membrane having a nitrogen-containing group such as a polyamide and aramid is easily damaged by free chlorine and thereby deteriorates the membrane separation efficiency such as the rejection and removing rates, it is important to perform the RO membrane treatment in a condition wherein free chlorine is not present. For this, Patent document 3 (JP H09-57067A) proposes to carry out the RO membrane treatment after sterilizing by a free chlorine agent and then eliminating the sterilizing agent by adding a reducing agent such as sodium bisulfite. In Patent document 3, the copper concentration is restricted because effect of elimination of sterilizing agent by addition of reducing agent is insufficient. It is suggested that elimination of free chlorine after sterilization by free chlorine agent is necessary.

Since, as above, a RO membrane, especially a RO membrane composed of a high molecular weight membrane having a nitrogen-containing group such as a polyamide and aramid is required to be used in a water system containing no free chlorine, residual chlorine should be removed from a feed water sterilized with a chlorine agent before being supplied to a RO membrane. If, however, the feed water is supplied to a RO membrane after the residual chlorine has been removed, slime will form as the treatment lasts to cause the deterioration of the membrane performance. In order to avert these problems, a combined chlorine agent as shown in Patent document 2 can be added in a free chlorine concentration of 0.1 m/L or lower. This method may be possible in the case that the combined chlorine agent is prepared on the spot to be added. However, when a combined chlorine agent prepared in a factory is added, after storage and transportation, on the spot so as to be diluted to a free chlorine concentration of 0.1 m/L or lower, there occurs a problem that the combined chlorine (total chlorine) concentration becomes low to decrease the slime prevention effect. Accordingly, there is a demand for a combined chlorine agent having a low concentration of free chlorine and a high concentration of combined chlorine.

Prior Technical Document

Patent Document

Patent document 1: JP H01-104310A
Patent document 2: JP2006-263510A
Patent document 3: JP H09-57067A

SUMMARY OF INVENTION

Problem to be Solved by Invention

An object of the present invention is to provide, in order to solve the above prior problem, a combined chlorine agent having a low concentration of free chlorine and a high concentration of combined chlorine whereby the combined chlorine concentration of water can be heightened when added to water systems at a low concentration of free chlorine. Another object of the present invention is to provide a method for producing the combined chlorine agent efficiently. A further object of the present invention is to provide a method of chlorine treatment under condition of a low free chlorine concentration.

Means to Solve Problem

The present invention consists in the following combined chlorine agent, method of production thereof and method of chlorine treatment;

(1) A combined chlorine agent consisting of an aqueous agent which comprises an alkali consisting of an alkali metal hydroxide, sulfamic acid, and oxidizing agent based on chlorine,
wherein the compositional ratio of the oxidizing agent based on chlorine to the sulfamic acid is in the range from 0.45 to 0.6 by Cl/N (mole ratio),
the compositional ratio of the oxidizing agent based on chlorine to alkali is in the range from 0.3 to 0.4 by Cl/alkali metal (mole ratio), and
the free chlorine concentration in the aqueous agent is 2% by weight or lower of the total chlorine concentration.

(2) The combined chlorine agent according to the above (1), wherein the combined chlorine agent is used for a slime control agent of a reverse osmosis membrane.

(3) A method of producing the combined chlorine agent according to the above (1) or (2), comprising
adding sulfamic acid to an aqueous solution of an alkali consisting of an alkali metal hydroxide to dissolve,
adding an oxidizing agent based on chlorine to the obtained sulfamic acid-alkali aqueous mixture, and
mixing the finally obtained aqueous mixture to form an aqueous solution agent.

(4) The method of producing the combined chlorine agent according to the above (3), wherein the aqueous solution of the alkali has a water content of 50-65% by weight.

(5) A method of chlorine treatment, comprising
adding the combined chlorine agent according to the above (1) to a water system so that the free chlorine concentration is 0.1 mg/L or lower.

(6) A method of chlorine treatment, comprising
adding the combined chlorine agent according to the above (1) to a feed water system to a reverse osmosis membrane so that the free chlorine concentration is 0.1 mg/L or lower.

According to the present invention, the free chlorine, combined chlorine, and total chlorine concentration are given in JIS K 0400-33-10:1999 and measured as $Cl_2$ concentration by the DPD method using N,N-diethyle-1,4-phenylenediamine. Free chlorine is defined as chlorine residing in a form of hypochlorous acid, hypochlorite ion or dissolved chlorine. Combined chlorine is defined as chlorine residing in a form of chloramine or organic chloramine which is measured by the DPD method but excluded from the free chlorine. Total chlorine is defined as chlorine in forms of free chlorine and/or combined chlorine.

A combined chlorine agent is an agent forming the above combined chlorine. The combined chlorine agent according to the present invention is an aqueous agent comprising an alkali consisting of an alkali metal hydroxide, sulfamic acid, and oxidizing agent based on chlorine. In the combined chlorine agent of the present invention, the compositional ratio of the oxidizing agent based on chlorine to the sulfamic acid in the aqueous agent is in the range from 0.45 to 0.6, preferably 0.45-0.55 by Cl/N (mole ratio), the compositional ratio of the oxidizing agent based on chlorine to alkali in the aqueous agent is in the range from 0.3 to 0.4, preferably 0.30-0.36 by Cl/alkali metal (mole ratio), and the free chlorine concentration in the aqueous agent is 2% by weight or lower of the total chlorine concentration. The aqueous solution agent is preferably at pH 13 or more and the compositional ratio of sulfamic acid to alkali in the aqueous solution agent is in the range from 0.5 to 0.7 by N/alkali metal (mole ratio). The above Cl/N (mole ratio) corresponds to the ratio of the $Cl_2$ mole number of the oxidizing agent (measured according to JIS K 0400-33-10:1999) to the mole number of sulfamic acid composed of N. The above N/alkali metal (mole ratio) corresponds to the ratio of the above mole number of sulfamic acid to the mole number of the alkali metal formed by the alkali metal hydroxide.

Sulfamic acid to form the combined chlorine agent is an amidosulfuric acid represented by $$R^1R^2NSO_3H \qquad [1]$$

wherein $R^1$, $R^2$ each denote H or a hydrocarbon group having a carbon number of 1-6 independently. A preferable sulfamic acid is the one, in a narrow sense, in which $R^1$, $R^2$ denote each H, while N-methyl sulfamic acid, N,N-dimethyl sulfamic acid, N-phenyl sulfamic acid, and so on may be used. The sulfamic acid may be used in the state of a free acid (in powder) or sulfamate such as an alkali metal salt including sodium salt and potassium salt.

An alkali for composing a combined chlorine agent consists of an alkali metal hydroxide such as sodium hydroxide and potassium hydroxide. An oxidizing agent based on chlorine includes hypochlorous acid, chlorous acid and water soluble salts thereof, such as an alkali metal salt thereof. These preferably have no content of sodium chloride. By controlling the sodium chloride content in the aqueous agent at 50,000 mg/L or lower, the precipitation of salt is prevented and stability of a halogenated oxidizing agent becomes increased.

The combined chlorine agent is produced by a method wherein sulfamic acid is added to an aqueous solution of an alkali consisting of an alkali metal hydroxide to dissolve, then an oxidizing agent based on chlorine is added to the obtained sulfamic acid-alkali aqueous mixture, and the finally obtained aqueous mixture is mixed to form an aqueous solution agent. The aqueous solution of the alkali preferably contains 50-65% by weight of water. The alkali consists of an alkali metal hydroxide such as sodium hydroxide and potassium hydroxide which maintains its solubility when the aqueous solution of the combined chlorine agent has formed.

Sulfamic acid may be added in a form of a sulfamate. Usable sulfamates include sodium sulfamate, potassium sulfamate and ammonium sulfamate, which are soluble when the aqueous solution of the combined chlorine agent has formed. Sulfamic acid is added in order that the sulfamic acid concentration in the aqueous solution agent becomes the above concentration. The amount of sulfamic acid to be added is preferably the amount wherein the compositional ratio of sulfamic acid to alkali is in the range from 0.5 to 0.7 by N/alkali metal (mole ratio). Sulfamic acid may be added in a form of a powder or aqueous solution of sulfamic acid or a sulfamate. In the case using a sulfamate, the amount of alkali metal contained in the sulfamate is calculated as an alkali. In the case using an aqueous solution, the amount of water contained in the aqueous solution is added as water in the aqueous solution of the alkali.

The oxidizing agent based on chlorine is preferably a hypochlorous acid or hypochlorite which is preferably added as an aqueous solution having an available chlorine ($Cl_2$) concentration of 5-20% by weight, preferably 10-15% by weight. The additive amount of the oxidizing agent based on chlorine is decided in order that the combined chlorine concentration in the aqueous solution agent becomes the above concentration as the available chlorine ($Cl_2$) concentration, and that the compositional ratio of the oxidizing agent based on the chlorine to sulfamic compound by Cl/N (mole ratio) becomes the above ratio, whereby a combined chlorine agent of an aqueous solution agent superior in reactivity, stability, handling and scentlessness of chlorine is produced efficiently, without foaming and emitting a chlorine odor. Here, oxidizing agent based on chlorine is preferably added and mixed gradually.

The combined chlorine agent according to the present invention as produced above is used by adding it to a water system for chlorine treatment. The agent has a low free chlorine concentration and high combined chlorine concentration, so that combined chlorine concentration of a water system to which the agent has been added can be heightened, even when added at a low free chlorine concentration. Since chlorine in the combined chlorine agent is in a form decided by the equilibrium between free chlorine and combined chlorine (total chlorine), it is presumed that, even in case of low free chlorine concentration, chlorine latently stored in a form of combined chlorine is released gradually to give an effect by a chlorine agent such as sterilization. Therefore, the water system added with the combined chlorine agent is put in a sterilization-active state so that slime forming is prevented. The combined chlorine agent can be added to a water system at a free chlorine concentration of 0.1 mg/L or lower to perform chlorine treatment. In this case, the total chlorine concentration may be 1-50 mg/L.

The combined chlorine agent according to the present invention is suitably used as a slime control agent for a RO membrane. The RO membrane is a permeation membrane for separating and removing solutes such as salts, organic matters and so on from water to be treated by reverse osmosis. RO membranes generally used for reverse osmosis membrane treatment are proper objects of the present invention. For the material of the RO membrane, the present invention is especially effective for a polymer membrane having a nitrogen-containing group, such as a polyamide (especially aromatic polyamide of low tolerance to chlorine), polyurea, and polypiperazine amide, while other RO membranes based on materials such as cellulose acetate may be applicable. The RO membrane may have a structure of a module, such as a spiral type, hollow fiber type, tubular type, and flat membrane type.

The water to be treated by the RO membrane treatment according to the present invention may be water containing contaminative substances. The water to be treated is subjected to a pretreatment for removing contaminative substances under the presence of free chlorine to cancel the contaminative power to a RO membrane and to control the free chlorine concentration to be 0.1 mg/L or lower, whereby the RO membrane treatment can be performed efficiently while preventing contamination and deterioration of the RO membrane. In order to control the free chlorine concentration of pretreated water at the above value, a reducing agent may be added to the pretreated water. According to the present invention, the water to be treated by the RO membrane is subjected to a chlorine treatment by adding the combined chlorine agent to control the free chlorine concentration to be 0.1 mg/L or lower, whereby slime control of the RO membrane can be performed. Here, the total chlorine concentration may be 1-50 mg/L.

Effect of Invention

According to the present invention, a combined chlorine agent having a low concentration of free chlorine and a high concentration of combined chlorine can be obtained, whereby the combined chlorine concentration can be heightened even if added at a low free chlorine concentration.

According to the method for producing the combined chlorine agent of the present invention, the combined chlorine agent can be produced efficiently.

According to the method of chlorine treatment of the present invention, chlorine treatment under the condition of a low free chlorine concentration can be performed by adding the above combined chlorine agent. In the case that the combined chlorine agent is used as a slime control agent for a RO membrane, slime control is performed without damage of the RO membrane whereby the RO membrane treatment can be carried out efficiently.

EMBODIMENT OF THE INVENTION

Below, the present invention is explained by way of Examples and Comparative Examples wherein % denotes "% by weight" and part denotes "part by weight" unless specific indication is given.

EXAMPLES

Examples 1-3

To pure water in amount shown for each Example in Table 1, sodium hydroxide was added to dissolve therein, then sulfamic acid (powdery sulfamic acid wherein $R^1$, $R^2$ in the above formula 1 are each H) was added to dissolve therein, and then sodium hypochlorite in the amount shown for each Example in Table 1 was added to dissolve therein whereby the combined chlorine agent of the aqueous solution agent of each Example was produced. Characteristics, free chlorine concentration and total chlorine concentration of the obtained aqueous solution agents are shown in Table 1. In Tables 1-4, NaOH (Na mol/L), N (mol/L) and available chlorine (mol/L) are shown as values, each calculated with the specific gravity of the solution being 1.3.

TABLE 1

|  | Example 1 | Example 2 | Example 3 |
|---|---|---|---|
| Main component | Comb. Cl agent | Comb. Cl agent | Comb. Cl agent |
| Pure water (part) | 15.5 | 13.2 | 8.6 |
| 48% NaOH (part) | 19.5 | 20.8 | 23.4 |
| Sulfamic acid (part) | 15.0 | 16.0 | 18.0 |
| 12% ($Cl_2$) NaClO (part) | 50.0 | 50.0 | 50.0 |
| Total (part) | 100 | 100 | 100 |
| NaOH (Na mol/L) | 3.043 | 3.246 | 3.651 |
| N (mol/L) | 2.009 | 2.143 | 2.411 |
| Available Cl (mol/L) | 1.099 | 1.099 | 1.099 |
| N/Na (mol ratio) | 0.66 | 0.66 | 0.66 |
| Cl/N (mol ratio) | 0.55 | 0.51 | 0.46 |
| Cl/Na (mol ratio) | 0.36 | 0.34 | 0.30 |
| pH (when prepared) | pH > 13 | pH > 13 | pH > 13 |
| Free Cl (when prepared) (mg/L) | <1000 | <1000 | <1000 |
| Total Cl (when prepared) (%) | 6.9 | 6.9 | 6.9 |
| Appearance (when prepared) | Good | Good | Good |
| pH (after 7 days storage at 40° C.) | pH > 13 | pH > 13 | pH > 13 |
| Free Cl (after 7 days storage at 40° C.) (mg/L) | 930 | 920 | 940 |
| Total Cl (after 7 days storage at 40° C.) (%) | 6.9 | 6.9 | 6.9 |
| Appearance (after 7 days storage at 40° C.) | Good | Good | Good |
| Appearance (after 7 days storage at −5° C.) | Good | Good | Good |

Comparative Examples 1-3

Examples 1-3 were pursued except that the composition of each component was changed as described in Table 2. The results of Comparative Examples 1-3 are shown in Table 2. In Comparative Example 1, two parts of benzotriazole was added as another component to a sum total amount of 100 parts which was shown with *1 in Table 2.

TABLE 2

|  | Comp. Example 1 | Comp. Example 2 | Comp. Example 3 |
|---|---|---|---|
| Main component | Comb. Cl agent | Comb. Cl agent | Comb. Cl agent |
| Pure water (part) | 6.7 | 12.4 | 6.6 |
| 48% NaOH (part) | 19.3 | 15.6 | 18.9 |
| Sulfamic acid (part) | 12.0 | 12.0 | 14.5 |
| 12% ($Cl_2$) NaClO (part) | 60.0 | 60.0 | 60.0 |
| Total (part) | 100 *1 | 100 | 100 |
| NaOH (Na mol/L) | 3.012 | 2.434 | 2.949 |
| N (mol/L) | 1.607 | 1.607 | 1.942 |
| Available Cl (mol/L) | 1.319 | 1.319 | 1.319 |
| N/Na (mol ratio) | 0.53 | 0.66 | 0.66 |
| Cl/N (mol ratio) | 0.82 | 0.82 | 0.68 |
| Cl/Na (mol ratio) | 0.44 | 0.54 | 0.45 |
| pH (when prepared) | pH > 13 | pH > 13 | pH > 13 |
| Free Cl (when prepared) (mg/L) | 6000 | 6000 | 2000 |
| Total Cl (when prepared) (%) | 7.7 | 7.7 | 7.7 |
| Appearance (when prepared) | Good | Good | Good |
| pH (after 7 days storage at 40° C.) | pH > 13 | pH > 13 | pH > 13 |
| Free Cl (after 7 days storage at 40° C.) (mg/L) | 8000 | — | — |
| Total Cl (after 7 days storage at 40° C.) (%) | 7.1 | — | — |
| Appearance (after 7 days storage at 40° C.) | Good | Good | Good |
| Appearance (after 7 days storage at −5° C.) | Good | Good | Good |

Comparative Examples 4-6

Examples 1-3 were pursued except that the composition of each component was changed as described in Table 3, wherein the sulfamic acid was not able to dissolve into the aqueous solution of pure water added with sodium hydroxide (shown as "Deposit"). The results of Comparative Examples 4-6 are shown in Table 3.

TABLE 3

|  | Comp. Example 4 | Comp. Example 5 | Comp. Example 6 |
|---|---|---|---|
| Main component | Comb. Cl agent | Comb. Cl agent | Comb. Cl agent |
| Pure water (part) | 6.6 | 4.0 | 6.7 |
| 48% NaOH (part) | 24.4 | 26.0 | 27.3 |
| Sulfamic acid (part) | 19.0 | 20.0 | 21.0 |
| 12% ($Cl_2$) NaClO (part) | 50.0 | 50.0 | 45.0 |
| Total (part) | 100 | 100 | 100 |
| NaOH (Na mol/L) | 3.808 | 4.057 | 4.260 |
| N (mol/L) | 2.545 | 2.678 | 2.812 |
| Available Cl (mol/L) | 1.099 | 1.099 | 0.989 |
| N/Na (mol ratio) | 0.67 | 0.66 | 0.66 |
| Cl/N (mol ratio) | 0.43 | 0.41 | 0.35 |
| Cl/Na (mol ratio) | 0.29 | 0.27 | 0.23 |
| pH (when prepared) | — | — | — |
| Free Cl (when prepared) (mg/L) | — | — | — |
| Total Cl (when prepared) (%) | — | — | — |
| Appearance (when prepared) | Deposit | Deposit | Deposit |
| pH (after 7 days storage at 40° C.) | — | — | — |
| Free Cl (after 7 days storage at 40° C.) (mg/L) | — | — | — |
| Total Cl (after 7 days storage at 40° C.) (%) | — | — | — |
| Appearance (after 7 days storage at 40° C.) | — | — | — |
| Appearance (after 7 days storage at −5° C.) | — | — | — |

Comparative Examples 7-8

Examples 1-3 were pursued except that the composition of each component was changed as described in Table 4, wherein the sulfamic acid was not able to dissolve into the aqueous solution of pure water added with sodium hydroxide. Results of Comparative Examples 7-8 ware shown in Table 4.

TABLE 4

|  | Comp. Example 7 | Comp. Example 8 |
|---|---|---|
| Main component | Comb. Cl agent | Comb. Cl agent |
| Pure water (part) | 13.6 | 9.0 |
| 48% NaOH (part) | 23.4 | 26.0 |
| Sulfamic acid (part) | 18.0 | 20.0 |
| 12% ($Cl_2$) NaClO (part) | 45.0 | 45.0 |
| Total (part) | 100 | 100 |
| NaOH (Na mol/L) | 3.651 | 4.057 |
| N (mol/L) | 2.411 | 2.678 |
| Available Cl (mol/L) | 0.989 | 0.989 |
| N/Na (mol ratio) | 0.66 | 0.66 |
| Cl/N (mol ratio) | 0.41 | 0.37 |
| Cl/Na (mol ratio) | 0.27 | 0.24 |
| pH (when prepared) | — | — |
| Free Cl (when prepared) (mg/L) | — | — |
| Total Cl (when prepared) (%) | — | — |
| Appearance (when prepared) | Deposit | Deposit |
| pH (after 7 days storage at 40° C.) | — | — |
| Free Cl (after 7 days storage at 40° C.) (mg/L) | — | — |
| Total Cl (after 7 days storage at 40° C.) (%) | — | — |
| Appearance (after 7 days storage | — | — |

TABLE 4-continued

| | Comp. Example 7 | Comp. Example 8 |
|---|---|---|
| at 40° C.) | | |
| Appearance (after 7 days storage at −5° C.) | — | — |

Figure 1:
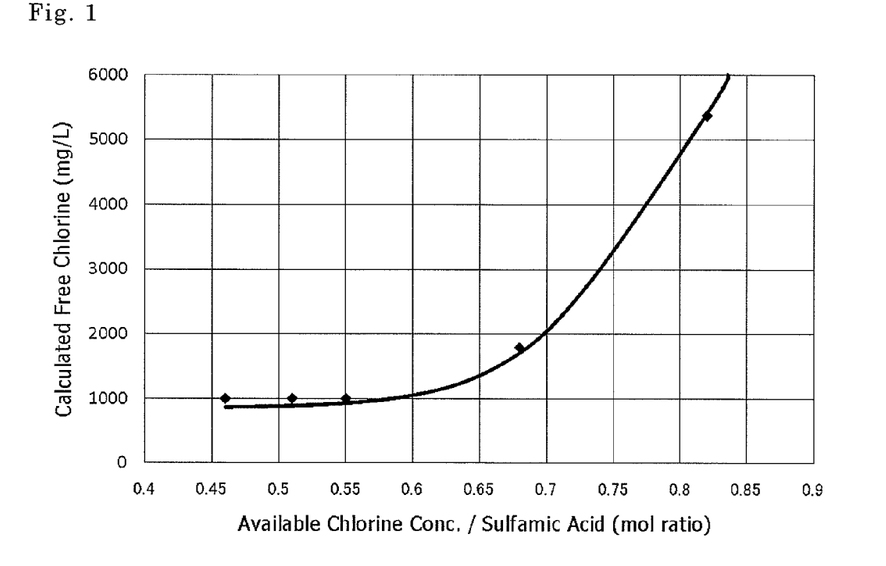
FIG. 1 is a graph showing the correlation between the Cl/N (mol ratio) and free chlorine concentration in Examples 1-3 and Comparative Examples 1-3.

In Examples 1-3 and Comparative Examples 1-3, the correlation between the Free chlorine concentration/Sulfamic acid (mol ratio), namely Cl/N (mol ratio) and Free chlorine concentration is shown in FIG. 1, wherein the free chlorine concentrations in Comparative Examples 1-3 were calculated so that the total chlorine concentration was 6.9%, the same as Examples 1-3.

The above results show that, in Examples 1-3, the free chlorine concentration in the aqueous agent is 1000 mg/L or lower, which falls in 2% by weight or lower of the total chlorine concentration, and that in Comparative Examples 1-3, the free chlorine concentration in the aqueous agent is higher than 1000 mg/L, which is higher than 2% by weight of the total chlorine concentration. Although the total chlorine concentration in Examples 1-3 is lower than in Comparative Examples 1-3, the difference in the total chlorine concentration is smaller than the difference in the free chlorine concentration. It is also shown that, in Comparative Examples 4-8, an aqueous agent cannot be produced because a deposit occurs.

Example 4

Cooling water discharged from a cooling tower was mixed with a combined chlorine agent and subjected to coagulation treatment, filtration and active carbon treatment to obtain a pretreated water having a total chlorine concentration of 5 mg/L and free chlorine concentration of 0.5 mg/L. The pretreated water was mixed with 10% by weight of an aqueous solution of sodium bisulfite, added at sodium bisulfite concentration of 15 mg/L, to reduce the total chlorine and free chlorine contained in the pretreated water to zero whereby the water to be treated was prepared. To this water to be treated, the combined chlorine agent obtained in Example 2 was added so that the total chlorine concentration was 1.2 mg/L and free chlorine concentration was 0.05 mg/L. The water to be treated was pressurized to 1.5 MPa by a pump and supplied to a concentrate room of a RO membrane treatment apparatus to carry out RO treatment. The RO membrane treatment apparatus was installed with a 4 inch spiral type RO membrane element of aromatic polyamide ("ES 20-D4" of Nitto Electric Industrial Co., Ltd) in a vessel.

Figure 2:
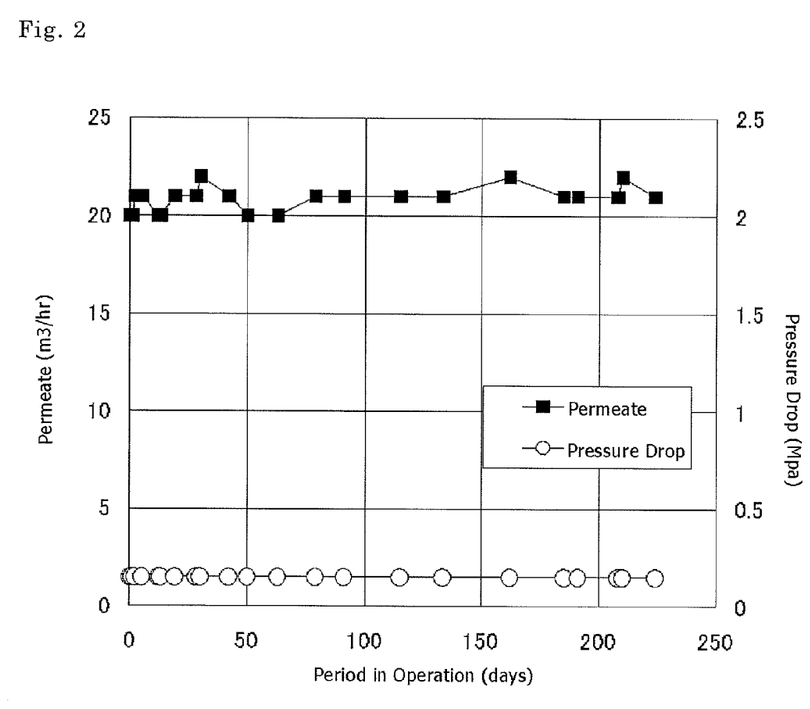
FIG. 2 is a graph showing the variations of permeate and pressure drop in Example 4.
Figure 3:
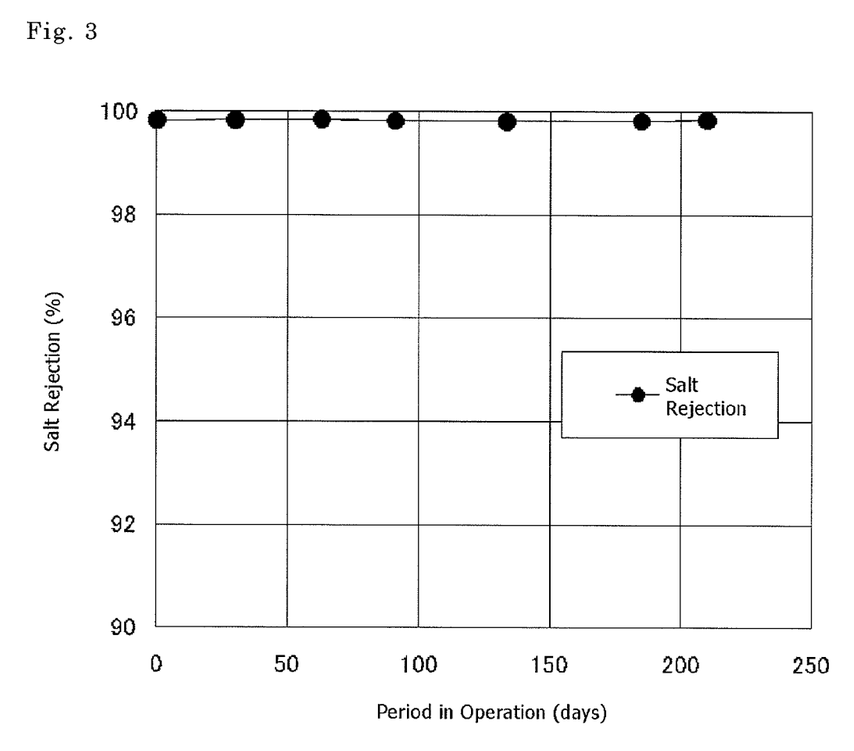
FIG. 3 is a graph showing the variation of salt rejection in Example 4.

During 3 months of continuous operation under the above condition, no deterioration of the RO membrane, no increase in pressure drop and no slime trouble occurred. During the period, variations of permeate and pressure drop are shown in FIG. 2 and variation of salt rejection is shown in FIG. 3 wherein it is affirmed that there occurs no clogging by slime because there is no increase in pressure drop and no decrease of flux since the start of the operation. Further, it is also affirmed that there occurs no deterioration in the water quality of the produced water by the adhesion of contaminants to the RO membrane or deterioration of the RO membrane because there occurs no decrease of salt rejection from the start of the operation.

Comparative Example 9

Figure 4:
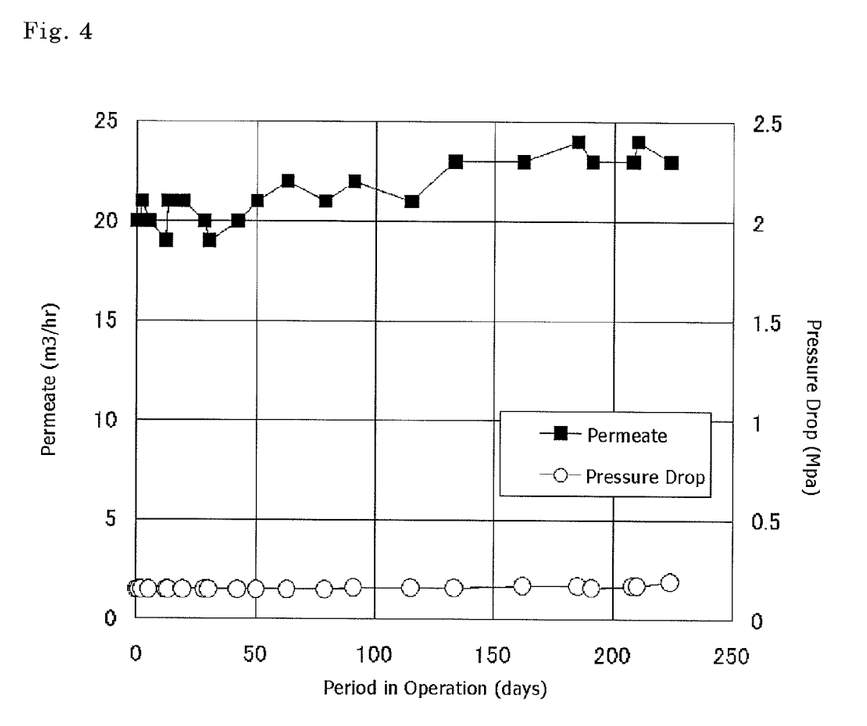
FIG. 4 is a graph showing the variation of permeate and pressure drop in Comparative Example 9.
Figure 5:
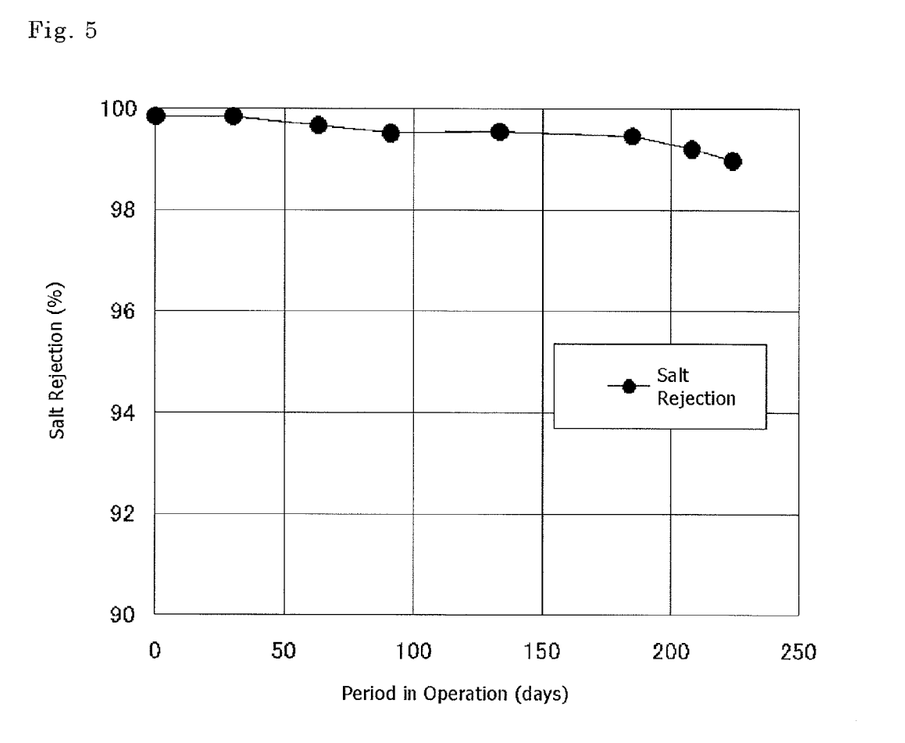
FIG. 5 is a graph showing the variation of salt rejection in Comparative Example 9.

Example 4 was pursued except that the pretreated water to be supplied to the RO membrane was further mixed with a chlorine agent so that the total chlorine concentration was 13 mg/L and free chlorine concentration 0.2 mg/L. In the period, the variation of permeate and pressure drop is shown in FIG. 4 and variation of salt rejection is shown in FIG. 5, wherein it is recognized that there occurs a deterioration in the RO membrane.

Comparative Example 10

Figure 6:
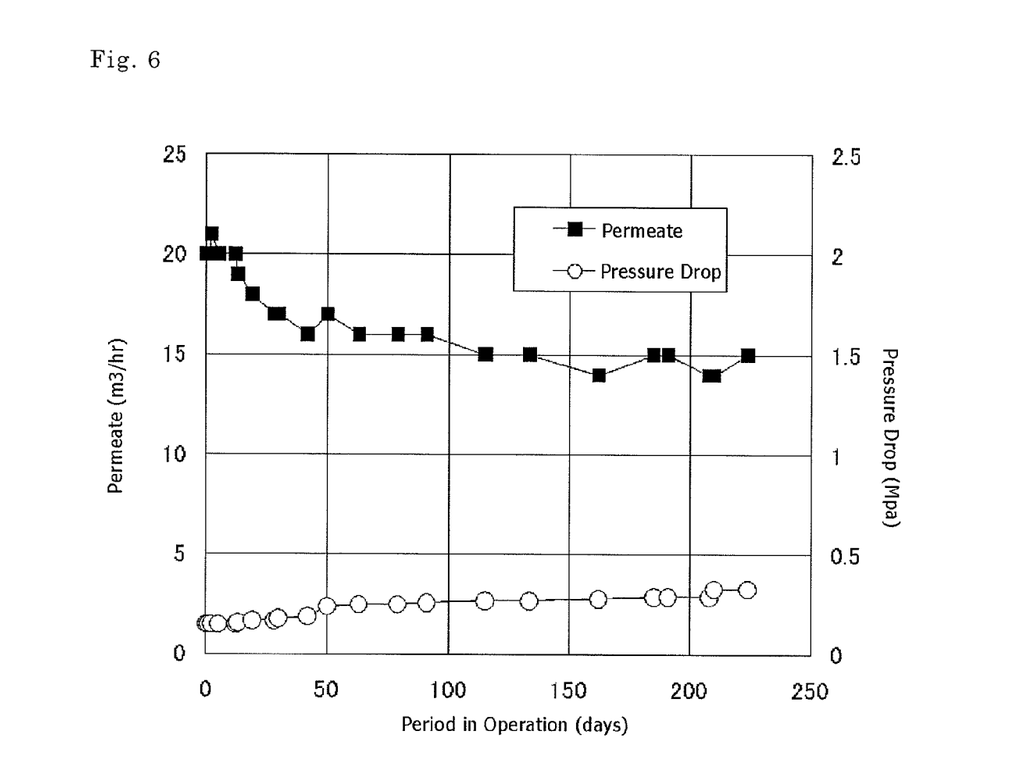
FIG. 6 is a graph showing the variation of permeate and pressure drop in Comparative Example 10.
Figure 7:
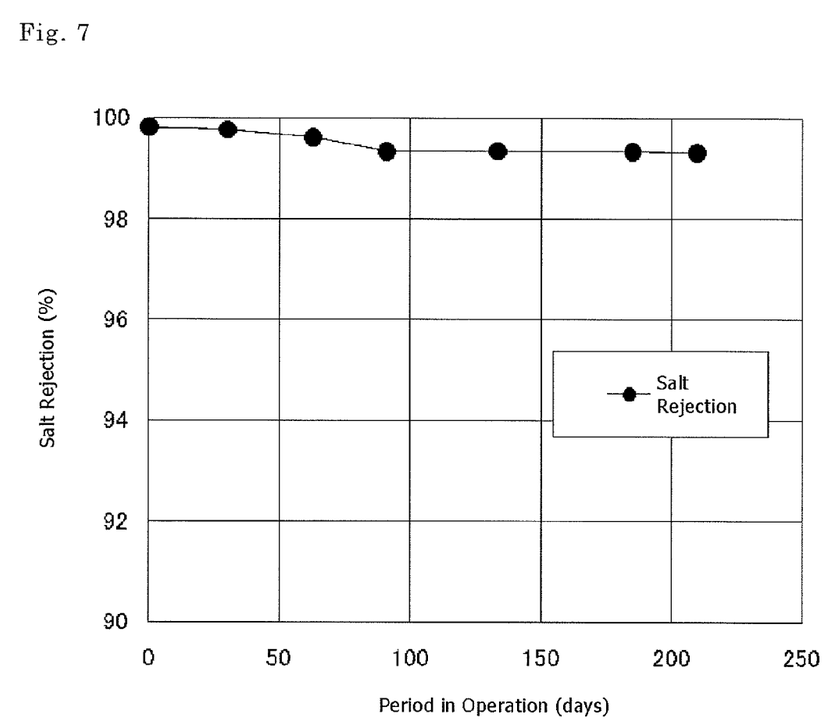
FIG. 7 is a graph showing the variation of salt rejection in Comparative Example 10.

Example 4 was pursued except that the water to be treated in the pretreatment was not mixed with a chlorine agent and that the pretreated water of a free chlorine concentration of 0.0 mg/L was supplied to the RO membrane. During the period, the variations in permeate and pressure drop are shown in FIG. 6 and variation of salt rejection is shown in FIG. 7, wherein it is recognized that there occurs a decrease in flux by slime formation.

INDUSTRIAL APPLICATION OF THE INVENTION

The present invention can be applied as a combined chlorine agent used for a slime control agent for a reverse osmosis membrane and used for other chlorine treatment agents, method of production thereof and method of chlorine treatment as the use thereof, especially a method of chlorine treatment for the slime control of a reverse osmosis membrane.

The invention claimed is:

1. A method of slime control for a reverse osmosis membrane, comprising the step of:
   adding a combined chlorine agent to a feed water system containing the reverse osmosis membrane, the combined chlorine agent comprising an aqueous agent containing an alkali comprising an alkali metal hydroxide, sulfamic acid or a salt thereof, and a chlorine-containing oxidizing agent,
   wherein the compositional ratio of the oxidizing agent to the sulfamic acid or salt thereof is in the range from 0.45 to 0.6 by Cl/N molar ratio,
   the compositional ratio of the oxidizing agent to alkali is in the range from 0.3 to 0.4 by Cl/alkali metal molar ratio,
   the compositional ratio of sulfamic acid or salt thereof to alkali in the aqueous solution agent is in the range from 0.5 to 0.7 by N/alkali metal molar ratio,
   the amount of alkali metal contained in the salt of sulfamic acid is calculated as alkali,
   the pH of the aqueous agent is 13 or more, and
   the free chlorine concentration in the aqueous agent is no more than 1000 mg/L and 2% by weight of the total chlorine concentration, and
   the chlorine agent is added to the feed water system containing the reverse osmosis membrane such that the free chlorine concentration in the feed water system is no more than 0.1 mg/L to prevent deterioration of the reverse osmosis membrane.

2. The method of slime control for a reverse osmosis membrane as claimed in claim 1, wherein the combined chlorine agent is added to the feed water system for the reverse osmosis membrane such that the free chlorine concentration is no more than 0.1 mg/L and total chlorine concentration is 1-50 mg/L.

3. The method of slime control for a reverse osmosis membrane as claimed in claim 1, wherein the reverse osmosis membrane is a polymer membrane having a nitrogen-containing group.

4. The method of slime control for a reverse osmosis membrane as claimed in claim 3, wherein the reverse osmosis membrane is a polyamide, polyurea or polypiperazine amide membrane.

5. The method of slime control for a reverse osmosis membrane as claimed in claim 1, wherein the combined chlorine agent consists of an alkali metal hydroxide, sulfamic acid or a salt thereof, a chlorine-containing oxidizing agent and water.

\* \* \* \* \*